United States Patent
Schreiber

(10) Patent No.: US 6,610,674 B1
(45) Date of Patent: Aug. 26, 2003

(54) METHOD OF TREATING INFLAMMATORY CONDITIONS WITH PROGESTERONE ANALOGS

(75) Inventor: Alan D. Schreiber, Philadelphia, PA (US)

(73) Assignee: University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/658,867

(22) Filed: Sep. 8, 2000

Related U.S. Application Data

(60) Provisional application No. 60/156,434, filed on Sep. 28, 1999.

(51) Int. Cl.$^7$ .............................................. A61K 31/56
(52) U.S. Cl. ....................... 514/177; 514/178; 514/181
(58) Field of Search ................................. 514/177, 178, 514/181

(56) References Cited

U.S. PATENT DOCUMENTS

| | | | |
|---|---|---|---|
| 4,439,432 A | * 3/1984 | Peat | 424/240 |
| 5,156,850 A | * 10/1992 | Wong et al. | 424/437 |
| 5,612,051 A | 3/1997 | Yue | 424/423 |

FOREIGN PATENT DOCUMENTS

| | | |
|---|---|---|
| DE | 2240187 A | 2/1974 |
| GB | 994547 A | 6/1965 |

OTHER PUBLICATIONS

Fossati, S. Minerva Ginecologica (Italy), (Oct. 31, 1970), 22(20), 993–995.*
Ackerman et al., Mast cells of psoriatic and atopic dermatitis skin are positive for TNF–α and degranulation is associated with Expression of ICAM–1 in the epidermis, Arch Dermatol Res 290(7): 353–9 (1998).
Akoum et al., Secretion of interleukin–6 by human endometriotic cells and regulation by proinflammatory cytokines and sex steroids, Human Reproduction 11: 2269–75 (1996).
Ameglio et al., Interleukin–11 production is increased in organ cultures of lesional skin of patients with active plaque–type psoriasis as compared with nonlesional and normal skin, Arch Dermatol Res 289(7): 399–403 (1997).
Baldassano et al., Inflammatory bowel disease in pediatric and adolescent patients, Gastroenterol Clin North Am 28(2): 445–58 (1999).
Bamberger et al., Dissociative glucocorticoid activity of medroxyprogesterone acetate in normal human lymphocytes, J of Clinical Endocrinology & Metabolism 84:4055–4061 (1999).
Barua et al., Effects of aging and sex steroids on the localization of T cell subsets in the ovary of chicken, *Gallus domesticus*, General and Comparative Endocrinology 114(1): 28–35 (1999).
Bond et al., Gastric emptying and gastric–intestinal transit in rats with varying ovarian hormone status, Nursing Res 45(4): 218–24 (1996).

Brochure, Questions & Answers About Crohn's Disease, Crohn's & Colitis Foundation of America (2000).
Brochure, Questions & Answers About Ulcerative Colitis, Crohn's & Colitis Foundation of America (2000).
Burkman, Noncontraceptive effects of hormonal contraceptives: Bone mass, sexually transmitted disease and pelvic inflammatory disease, cardiovascular disease, menstrual function, and future fertility, American Journal of Obstetrics and Gynecology 170: 1569–75 (1994).
Bussel et al., Immune thrombocytopenic purpura, neonatal alloimmune thrombocytopenia and post–transfusion purpura, Hematology: basic principles and practice 1849–1870 (1995).
Centocor, Inc., Remicade™ (Infliximab) Prescribing Information (1999).
Chang et al., Disturbed small intestinal motility in the late rat pregnancy, Gynecologic and Obstetric Investigation 45:221–224 (1998).
Chen et al., Effects of sex steroid hormones on gastric emptying and gastrointestinal transit in rats, Am J Physiol 268 (1): G171–6 (1995).
Correale et al, Steroid hormone regulation of cytokine secretion by proteolipid protein–specific CD4+ T cell clones isolated from multiple sclerosis patients and normal control subjects, The Journal of Immunology 161: 3365–3374 (1998).
Critchley et al, Role of inflammatory mediators in human endometrium during progesterone withdrawal and early pregnancy, Journal of Clinical Endocrinology and Metabolism 84: 240–48 (1999).
Cullins, Noncontraceptive benefits and therapeutic uses of depot medroxyprogesterone acetate, The Journal of Reproductive Medicine 41: 428–33 (1996).
Cushman et al., Hormone replacement therapy, inflammation, and hemostatis in elderly women, Arteriosclerosis, Thrombosis, and Vascular Biology 19: 893–99 (1999).
Day et al., Heparin, cell adhesion, and pathogenesis of inflammatory bowel disease, Lancet 354(9172): 62–5 (1999).
Déchaud et al., Evaluation of endometrial inflammation by quantification of macrophages, T lymphocytes, and interleukin–1 and –6 in human endometrium, Journal of Assisted Reproduction and Genetics 15: 612–18 (1998).

(List continued on next page.)

*Primary Examiner*—Sreeni Padmanabhan
*Assistant Examiner*—S. Jiang
(74) *Attorney, Agent, or Firm*—Finnegan, Henderson, Farabow, Garrett & Dunner, L.L.P.

(57) ABSTRACT

The present invention provides methods for treating inflammatory conditions, including but not limited to, inflammatory bowel disease (ulcerative colitis, Crohn's disease, and proctitis), other noninfectious, inflammatory conditions of the GI tract (microscopic colitis, allergic eosinophilic gastroenteritis, food allergies, pill induced esophagitis, celiac disease, recurrent polyps, and hemorrhoids), and psoriasis, using progesterone or progesterone analogs such as medroxyprogesterone acetate.

7 Claims, No Drawings

OTHER PUBLICATIONS

Duncan et al., An in vivo study of the action of antiglucocorticoids on thymus weight ratio, antibody titre, and the adrenal–pituitary–hypothalamus axis, J. Steroid Biochemistry 10:245–59 (1979).

Elkayam et al., Serum levels of IL–10, IL–6, IL–1ra, and sIL–2R patients with psoriatic arthritis, Rheumatoid Int 19(3): 101–5 (2000).

Frannson et al., Psoriatic fibroblasts secrete lower amounts of IL–6 than healthy fibroblasts before and after stimulation with TNF–alpha, Arch Dermatol Res 291(10): 538–41 (1999).

Friedman et al., Effect of estradiol and Steroid Analogues on the Clearance of Immunoglobulin G–coated Erythrocytes, J. Clin. Invest. 75: 162–167 (1985).

Friend et al., Drug glycosides: potential prodrugs for colon-–specific drug delivery, J. Med. Chem. 28:51–57 (1985).

Furukawa et al., Platelet–activating factor–induced ischemic bowel necorsis: the effect of platelet–activating factor acetylhydrolase, Pediatric Research 34: 237–41 (1993).

Futamura, Effects of medroxyprogesterone acetate and β–estradiol on interleukin–6 production from osteoblasts and bone marrow macrophages of wistar rats of different ages, The Journal of Toxicological Sciences 20: 155–60 (1995).

Galati et al., Gastric emptying and orocecal transit in portal hypertension and end–stage chronic liver disease, Liver Transpl Surg 3(1): 34–8 (1997).

Gelfand, Ischemic colitis associated with a depot synthetic progestogen, Digestive Diseases 17: 275–77 (1972).

Gomez et al., Treatment with progesterone analogues decreases macrophage Fcy receptors expression, Clinical Immunology and Immunopathology 89: 231–39 (1998).

Goth, A.., Medical Pharmacology, C.V. Mosby Co., St. Louis, p. 429 (1966).

Gunthert, Importance of CD44 variant isoforms in mouse models for inflammatory bowel disease, Mechanisms of B Cell Neoplasia :307–13 (Melchers et al., eds. 1998).

Guthrie et al., The in vivo glucocorticoid and antiglucocorticoid actions of medroxyprogesterone acetate, Endocrinology 107:1393–1396 (1980).

Hamano et al, Effect of sex hormones on eosinophilic inflammation in nasal mucosa, Allergy and Asthma Proceedings 19: 263–269 (1998).

Hanauer, Inflammatory bowel disease, The New England Journal of Medicine 334: 841–848 (1996).

Heitkemper et al., Gastric motility in rats with varying ovarian hormone status, West J Nurs Res 17(1): 9–19 (1995).

Heitkemper et al., Pattern of gastrointestinal and somatic symptoms across the menstrual cycle, Gastroenterology 102: 505–13 (1992).

Hori et al., Differential effects of angiostatic steroids and dexamethasone on angiogenesis and cytokine levels in rat sponge implants, British Journal of Pharmacology 118:1584–91 (1996).

Hugot et al., Etiology of the inflammatory bowel diseases, Int J Colorectal Dis 14(1): 2–9 (1999).

Jackson et al., Modulation of angiogenesis in a model of chronic inflammation, Inflammation Research 46: S129–S130 (1997).

Kaluza et al., Different transcriptional activity and In Vitro TNF–alpha production in psoriasis patients carrying the TNF–alpha 238A promoter polymorphism, J Invest Dermatol 114(6): 1180–3 (2000).

Koh et al., Effects of hormone therapy on inflammatory cell adhesion molecules in postmenopausal healthy women, The American Journal of Cardiology 80: 1505–07 (1997).

Kubo et al., Regulation of histamine synthesis in mouse CD4+ and CD8+ T lymphocytes, Inflamm Res 48(3): 149–53 (1999).

Lapp et al., Modulation by progesterone of interleukin–6 production by gingival fibroblasts, Journal of Periodontology 66: 279–84 (1995).

Lee et al., Medroxyprogesterone acetate and dexamethasone are competitive inhibitors of different human steroidogenic enzymes, The Journal of Clinical Endocrinology & Metabolism 84: 2104–10 (1999).

Marshall et al., Hormonal therapy for bleeding gastrointestinal mucosal vascular abnormalities: a promising alternative, Eur J Gastroenterol Hepatol 9(5): 521–5 (1997).

Marshall et al., Putting rectal 5–aminosalicylic acid in its place: The role in distal ulcerative colitis, Am. J. Gastroenterology, 95:1628–1636 (2000).

Mathias et al., Effect of leuprolide acetate in patients with moderate to severe functional bowel disease, Digestive Dis Sci 39(6):1155–62 (1994).

Mathias et al., Relationship of reproductive hormones and neuromuscular disease of the gastrointestinal tract, Digestive Diseases 16:3–13 (1998).

Mazure et al., Successful treatment of retractile mesenteritis with oral progesterone, Gasteroenterology 114: 1313–17 (1998).

Murad et al., Estrogens and progestins, Goodman and Gilman's The Pharmacological Basis of Therapeutics 1433–1438 (1980).

Nagpaul et al., Effect of medroxyprogesterone acetate on the intestinal absorptive functions in protein–deficient rat, Biochemistry International 8: 739–48 (1984).

Nagpaul et al., Effect of various doses of medroxyprogesterone acetate on intestinal functions in rats, Indian Journal of Gastroenterology, 9: 45–47 (1990).

Oh et al., Differential effects of progesterone and its analogues on the contractility of the murine jejunum in vitro, Journal of Surgical Research 75(1): 1–5 (1998).

Oh et al., Treatment with anti–tumor necrosis factor alpha (TNF–α) monoclonal antibody dramatically decreases the clinical activity of psoriasis lesions, J. Am. Acad. Dermatol., 42:829–30 (2000).

Okubo et al., Peripheral blood monocytes in psoriatic patients overproduce cytokines. J. Dermatol. Sci., 17:223–32 (1998).

Papadakis et al., Current theories on the causes of inflammatory bowel disease, Gastroenterol Clin North Am 28:283–296 (1999).

Patel et al., Cytokine production in pouchitis is similar to that in ulcerative colitis, Diseases of the Colon & Rectum 38(8): 831–7 (1995).

Powrie et al., Inhibition of Th1 responses prevents inflammatory bowel disease in scid mice reconstituted with $CD45RB^{hi}$ $CD4^+$ T Cells, Immunity 1:553–562 (1994).

Ritchlin et al., Patterns of cytokine production in psoriatic synovium, J. Rheumatol 25:1544–53 (1998).

Rubenstein, Microbially controlled drug delivery to the colon, Biopharm & Drug Dispos. 11:465–475 (1990).

Salyers et al., Cellular location of enzymes involved in chondroitrin sulfate breakdown by *Bacteroides thetaiotaomicron,* J. Bacteriol 143:772–780 (1980).

Sandborn et al., Antitumor necrosis factor therapy for inflammatory bowel disease: A review of agents, pharmacology, clinical results, and safety, Inflammatory Bowel Disease 5:119–33 (1999).

Sands, Novel therapies for inflammatory bowel disease, Gastroenterol Clin North Am 28(2): 323–51 (1999).

Schacter et al., Megestrol acetate: clinical experience, Cancer Treatment Reviews 16: 49–63 (1989).

Schreiber et al., Effect of endogenous and synthetic sex steroids on the clearance of antibody–coated cells, The Journal of Immunology 141(9): 2959–2966 (1988).

Schreiber, Clinical immunology of the corticosteroids in Progress in Clinical Immunology 3: 103–14 Robert S. Schwartz, M.D. ed. (1977).

Schreiber, Immunohematology, JAMA 248: 1380–85 (1982).

Seishima et al., Increased serum soluble Fas, tumor necrosis factor alpha and generalized pustular psoriasis, Dermatology 196(3): 371–2 (1988).

Singh et al., Alterations and reversibility of digestive and absorptive functions of rat intestine following medroxyprogesterone acetate administration, Biochemistry International 8(3): 453–62 (1984).

Singh et al., Effect of medroxyprogesterone acetate on the digestive and absorptive functions of rat intestine, Digestion 28: 234–39 (1983).

Stein et al., Medical therapy for inflammatory bowel disease, Gastroenterol Clin North Am 28(2): 297–321 (1999).

Stenson., Inflammatory Bowel Disease, Cecil Textbook of Medicine 1($21^{st}$ ed.): 722–729 (2000).

Terajima et al., An important role of tumor necrosis factor–alpha in the induction of adhesion molecules in psoriasis, Arch Dermatol Res 209(5): 246–52 (1998).

Terenius, Affinities of progestogen and estrogen receptors in rabbit uterus for synthetic progestogens, Steroids 23:909–919 (1974).

Walsh et al., Progesterone and estrogen are potential mediators of gastric slow–wave dysrhythmias in nausea of pregnancy, Am J Physiol 270 (3): G506–14 (1996).

Ward et al., Clinical Economics Review: Medical Management of Inflammatory Bowl Disease, Ailment Pharmacol Ther 13:15–25 (1999).

Wurzer et al., Hormonal therapy in chronic radiation colitis, Am J Gastroenterol 93(12): 2536–8 (1998).

Zanger et al., Divergent effects of hormone therapy on serum markers of inflammation in postmenopausal women with coronary artery disease on appropriate medical management, J Am Coll Cardiol 36:1797–1802 (2000).

Nakagawa, et al. "Anti–Inflammatory Action of Progesterone and its Possible Mode of Action in Rats," Biochemical Pharmacology, 30(6): 639–644 (1981).

Haney, et al., "Reduction of the Intraperitoneal Inflammation Associated with Endometriosis by Treatment of Medroxyprogesterone Acetate," American Journal of Obstetrics and Gynecology, 159 (2): 450–454 (1988).

Reynolds, et al, "Pharmacotherapy of Inflammatory Bowel Disease," Digestive Diseases and Sciences, 11 (6): 334–342 (1993).

Murch, et al. "Medical Management of Chronic Inflammatory Bowel Disease", Baillieres Clinical Gastroenterology, GB, Baillieres Tindall, 8 (1): 133–148 (1994).

Eliakim, et al., "Estrogen, Progesterone and the Gastrointestinal Tract," Journal of Reproductive Medicine 45 (10): 781–788 (2000).

* cited by examiner

METHOD OF TREATING INFLAMMATORY CONDITIONS WITH PROGESTERONE ANALOGS

PRIORITY INFORMATION

This application claims priority to U.S. Provisional Patent Applications No. 60/156,434 filed Sep. 28, 1999.

TECHNICAL FIELD

This invention provides methods for treating inflammatory conditions, including but not limited to, inflammatory bowel disease (ulcerative colitis, Crohn's disease, and proctitis), other noninfectious, inflammatory conditions of the GI tract (microscopic colitis, allergic eosinophilic gastroenteritis, food allergies, pill induced esophagitis, celiac disease, recurrent polyps, and hemorrhoids), and psoriasis using progesterone and progesterone analogs.

BACKGROUND OF THE INVENTION

Inflammatory Bowel Disease

"Inflammatory bowel disease" (IBD) encompasses the idiopathic, chronic inflammatory bowel diseases ulcerative colitis (UC), Crohn's disease (CD), and proctitis. Researchers do not know the cause of these diseases, but believe that they involve genetic and immunologic influences on the gastrointestinal tract's ability to distinguish foreign from self-antigens and/or to alter the mucosal immune response. They share many overlapping epidemiological, clinical, and therapeutic features. IBD affects up to 1,000,000 Americans and disease symptoms can be so severe as to prevent the patient from carrying on a normal life. The total cost of the disease, including lost productivity, in the US is two billion dollars per year. Ward et al., Clinical economics review: medical management of inflammatory bowel disease, *Ailment Pharmacol Ther* 13:15–25 (1999). Drug therapies that allow patients to avoid surgical intervention could reduce the cost significantly.

IBD (UC, CD, and proctitis) is different from spastic colon or irritable bowel syndrome, which is a motility disorder of the gastrointestinal tract. UC is characterized by a diffuse, continuous, superficial, ulcerative inflammation of the colon, not due to any known single cause. The inflammation often begins within the rectum and extends proximally into the bowel. UC affects the inner mucosal layer of the colon (lamina propria) in a continuous manner, with no portions of healthy tissues between the diseased areas. Additionally, it affects only the colon, not other areas of the gastrointestinal (GI) tract, except in rare instances. UC may be accompanied by bloody diarrhea, constipation, very frequent bowel movements (often 15 to 20 per day), explosive diarrhea, rectal incontinence, pus, mucus, gas, fever, tachycardia, weakness, and anemia. UC creates striking changes in the mucosa and submucosa of the colon and rectum. The disease causes diffuse severe ulceration, inflammation, and congestion of the lining of the colon and rectum. More severe disease states include thinning of the bowel, susceptibility to ulcers, fibrosis, contraction, and narrowing of the intestinal lumen.

CD is characterized by focal, asymmetric, transmural inflammation affecting any portion of the gastrointestinal tract from the mouth to the anus. The ileum and right colon are, however, most often involved. CD affects all layers of the intestine, but there can be patches of normal bowel in between the diseased regions. Depending on where in the bowel the disease manifests itself, CD can cause nausea vomiting, epigastric pain, diarrhea, cramping abdominal pain, rectal bleeding, loss of appetite, fever, night sweats, malaise, arthralgias, and weight loss.

Proctitis, inflammation of the rectum, is invariably present in UC and is sometimes present in CD. It may also occur independently from these diseases. Proctitis is another manifestation of IBD with pathology similar to UC. A patient presenting with proctitis may later develop full-blown UC or CD.

Physicians and medical researchers have not been successful in identifying a cause for these diseases, although several theories have been postulated. The diseases may be caused by a pathogen or other antigen that initiates the inflammatory response in the bowel, accompanied by a defect in the ability to down-regulate the immune response. Once initiated, many of the pathophysiological events in IBD are related to amplification of the inflammatory process. In response to antigens, cytokines and other inflammatory mediators are released. Some cytokines promote T cell activity. The inflammatory cascade continues with IL-2, helper T cells, B-cell proliferation, and antibody synthesis. Stimulated neutrophils and macrophages accumulate and further damage the tissue by releasing reactive oxygen species and other biologically active products. Additional acute inflammatory cells respond to the tissue damage, whether or not the primary initiating stimulus has ceased.

Other research on IBD suggests that abnormalities in the immune system, nonimmune cells in the intestinal mucosa, genetic risk determinants, and random environmental factors may all be necessary to induce IBD. Papadakis et al., Current Theories on the Causes of Inflammatory Bowel Disease, *Gastroenterol Clin North Am* 28:283–296 (1999). Researchers have also postulated that tumor necrosis factor-$\alpha$ (TNF-$\alpha$), a proinflammatory cytokine, may play an important role in the pathogenesis of inflammatory bowel disease. Sanborn et al, Antitumor necrosis factor therapy for inflammatory bowel disease: a review of agents, pharmacology, clinical results, and safety, *Inflamm Bowel Dis* 5:119–33 (1999). The uncertainty about the cause of IBD has lead to confusion about the appropriate treatment strategy.

Currently, no treatment exists that will cure or effectively manage both forms of inflammatory bowel disease. Present treatments include aminosalicylates (sulfasalazine, mesalamine), glucocorticoids (hydrocortisone, prednisone), antibiotics (to reduce secondary infection), immunosuppressants (6-mercaptopurine, cyclosporine), belladonna, atropine, and phenobarbital. Immunosuppressants (6-mercaptopurine, azathioprine, FK-506/tacrolimus) and neuroimmunomodulation agents (somatostatin, substance P, local anesthetics) have also been used as therapy for IBD. Prevention of adhesion and recruitment has been suggested by using antisense oligonucleotides to ICAM-1. Other miscellaneous therapies that have been suggested include arachidonic acid metabolites, anti-free radicals, short-chain fatty acids, nicotine, bismuth, ketotifen, heparin, interferon-$\alpha$, chloroquinone/hydroxychloroquine, hyperbaric oxygen, IV immunoglobulin, and leukapheresis. Sands, Novel Therapies for Inflammatory Bowel Disease, *Inflammatory Bowel Disease* 28:323–351 (1999).

Infliximab, an anti-TNF-$\alpha$ antibody, has recently been developed as a treatment for Crohn's disease, because overproduction of TNF-$\alpha$ leads to inflammation. Biological activities attributed to TNF-$\alpha$ include induction of proinflammatory cytokines such as IL-1 and IL-6, enhancement of leukocyte migration by increasing endothelial layer permeability and expression of adhesion molecules by endothelial cells and leukocytes, and activation of neutrophil and eosinophil functional activity. REMICADE™ (Infliximab) Prescribing Information.

Additional medical management strategies include psychotherapy, diet control, fluid and electrolytes. A significant number of patients must resort to surgical removal of the affected portion of the bowel. None of the known therapies provide successful long term treatment for all patients, and many of the therapies have serious side effects. For example, patients treated with steroid drugs, such as glucocorticoids, can develop diabetes, hypertension, psychological changes, Cushings syndrome, changes in protein metabolism, osteoporosis, cataracts, avascular hip necrosis, and infection. Patients taking immunosuppressants run serious risk of infection and may have an increased incidence of cancer.

Other Noninfectious, Inflammatory Conditions of the GI Tract

Improved treatments are also needed for other noninfectious, inflammatory conditions of the GI tract, including but not limited to microscopic colitis, allergic eosinophilic gastroenteritis, food allergies, pill induced esophagitis, celiac disease, recurrent polyps, and hemorrhoids.

Microscopic colitis is another form of colitis, where only microscopic changes are seen in the GI tract tissue. No gross clinical manifestations are visible upon colonoscopy. Patients with microscopic colitis commonly have diarrhea.

Allergic eosinophilic gastroenteritis can be diagnosed upon biopsy of the GI tract tissue, which will show predominantly eosinophilic infiltration of the bowel wall. This inflammatory condition is induced by an allergic reaction to food, microbes, or other ingested substance that come in contact with the bowel wall. Cramping pain, diarrhea, and weight loss are common. This condition is often treated with prednisone. Food allergies can also cause other inflammatory conditions in the GI tract, and are often treated with steroid hormones, such as the glucocorticoids.

Pill-induced esophagitis is an inflammatory condition of the esophagus caused when a pill becomes lodged in the esophagus during swallowing. The inflammatory condition can continue even after the pill becomes dislodged.

Celiac disease is an inflammatory condition of the small intestine, precipitated by the ingestion of wheat, rye, and barley, in individuals sensitive or allergic to these foods. While sensitive individuals can try to avoid these foods, it is very difficult to prevent accidental ingestion, and patients very often require treatment. Symptoms of celiac disease include diarrhea, bloating, and discomfort.

Recurrent polyps are also thought to have an inflammatory component, with inflammation in the colon and around the polyps. Polyps are a serious, precancerous GI condition, and are generally removed surgically. A treatment is needed to prevent polyps from recurring or treat them without surgical intervention.

Hemorrhoids, enlarged and inflamed veins in the wall of the anus, are usually a consequence of prolonged constipation or diarrhea. The inflammatory process affects the veins and the tissues surrounding the veins. Hemorrhoids can occur with IBD (UC, CD, and proctitis) and may also occur independently of these diseases. This inflammatory condition of the GI tract can be treated with anti-inflammatory steroid drugs, such as glucocorticoids, or surgery.

Psoriasis

Psoriasis, another inflammatory condition, affects more than 7 million Americans. It is a noncontaigious skin disorder that most commonly appears as inflamed swollen skin lesions covered with silvery white scale. The exact cause of psoriasis is not known, but a patient's keratinocytes grow as if there was a wound, in a regenerative maturation process. The skin cannot shed the extra cells fast enough, and excessive skin cells build up and form elevated, scaly lesions. Psoriasis occurs in several forms including: plaque psoriasis, guttate psoriasis, inverse psoriasis, erythrodermic psoriasis, pustular psoriasis, psoriatic arthritis, scalp psoriasis, and nail psoriasis.

Various treatment strategies have been used for psoriasis, though none are completely effective. Topical steroid medications are one of the most common therapies prescribed. Steroids can also be injected into the lesions. Topical retinioids have also been useful. Phototherapy offers a second level of treatment for more persistent cases. The third level of treatment includes systemic drugs such as methotrexate, oral retinoids, and cyclosporin.

Recent research has suggested that psoriasis may respond to treatment with an anti-TNF-α monoclonal antibody. Oh, C. J., et al., Treatment with anti-tumor necrosis factor alpha (TNF-α) monoclonal antibody dramatically decreases the clinical activity of psoriasis lesions, *J. Am. Acad. Dermatol.*, 42:829–30 (2000). Elevated levels of TNF-α have been associated with psoriasis, especially psoriatic arthritis and psoriasis vulgaris. Ritchlin C., et al., Patterns of cytokine production in psoriatic synovium, *J. Rheumatol.*, 25:1544–52 (1998); Okubo Y, et al., Peripheral blood monocytes in psoriatic patients overproduce cytokines, *J. Dermatol. Sci.*, 17:223–32 (1998).

Medroxyprogesterone Acetate

Medroxyprogesterone acetate is a derivative of progesterone and is a white, odorless crystalline powder, stable in air, melting between 200° and 210° C. The chemical name for medroxyprogesterone acetate is pregn-4-ene-3,20-dione, 17-(acetyloxy)-6-methyl-, (6α)-. Its structural formula is as follows:

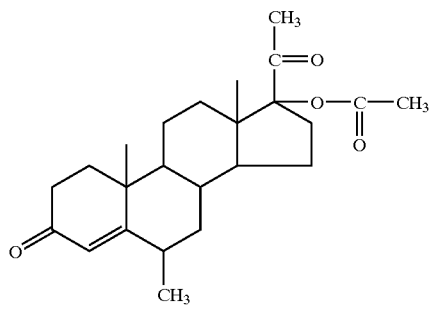

Medroxyprogesterone acetate is currently prescribed for secondary amenorrhea, abnormal uterine bleeding due to hormonal imbalance, and contraception. Medroxyprogesterone acetate has also been combined with estrogens for treatment of menopausal symptoms. Medroxyprogesterone acetate, acting through its regulation of the menstrual cycle, can also be used for reduced iron-deficiency anemia, protection against pelvic inflammatory disease, protection from endometrial cancer, and improved hematologic parameters among users with sickle cell disease. Cullins, Noncontraceptive Benefits and Therapeutic Uses of Depot Medroxyprogesterone Acetate, *Journal of Reproductive Medicine*, 41:428–433 (1996). Thus, it is surprising that the administration of progesterone or progesterone analogs is effective in the treatment of inflammatory conditions, including but not limited to, inflammatory bowel disease (ulcerative colitis, Crohn's disease, and proctitis), other noninfectious, inflammatory conditions of the GI tract (microscopic colitis, allergic eosinophilic gastroenteritis, food allergies, pill induced esophagitis, celiac disease, recurrent polyps, and hemorrhoids), and psoriasis.

SUMMARY OF THE INVENTION

It is an object of the present invention to provide a method for treating a patient suffering from at least one of the following conditions: inflammatory conditions, including but not limited to, inflammatory bowel disease (ulcerative colitis, Crohn's disease, and proctitis), other noninfectious, inflammatory conditions of the GI tract (microscopic colitis, allergic eosinophilic gastroenteritis, food allergies, pill induced esophagitis, celiac disease, recurrent polyps, and hemorrhoids), and psoriasis wherein a progesterone or progesterone analog is administered to the patient.

It is an object of the present invention to provide a method for treating a patient suffering from inflammatory conditions, including but not limited to, inflammatory bowel disease (ulcerative colitis, Crohn's disease, and proctitis), other noninfectious, inflammatory conditions of the GI tract (microscopic colitis, allergic eosinophilic gastroenteritis, food allergies, pill induced esophagitis, celiac disease, recurrent polyps, and hemorrhoids), and psoriasis, wherein medroxyprogesterone acetate is administered to the patient.

DETAILED DESCRIPTION OF THE INVENTION

The present invention relates to a method for treating a patient suffering from at least one of the following inflammatory conditions, including but not limited to, inflammatory bowel disease (ulcerative colitis, Crohn's disease, and proctitis), other noninfectious, inflammatory conditions of the GI tract (microscopic colitis, allergic eosinophilic gastroenteritis, food allergies, pill induced esophagitis, celiac disease, recurrent polyps, and hemorrhoids), and psoriasis, wherein progesterone or a progesterone analog is administered to the patient.

Progesterone analogs for use in the invention include, but are not limited to: acetophenone derivative of 16α, 17α-dihydroxyprogesterone, allyestrenol, chlormadinone acetate, cyproterone acetate, desogestrel, dimethisterone, dydrogesterone, esthisterone, estrenols, ethinylestrenol, ethlestrenol, ethynodiol diacetate, hydroxyprogesterone caproate, medroxyprogesterone acetate, megestrol acetate, norethandrolone, norethindrone, norethindrone enanthate, norethisterone, norethynodrel, norgestimate, norgestrel, 19-nortestosterone, and valerate and caproate esters of progesterone.

In one embodiment of the invention, the progesterone analog is medroxyprogesterone acetate. Other embodiments include medroxyprogesterone and its other salts and derivatives. While not wishing to be bound by any theory, it is believed that during IBD and other noninfectious, inflammatory conditions of the bowel, lymphocytes may infiltrate the bowel, drawn there by a cytokine or other chemotactic or inflammatory mediators. Progesterone and progesterone analogs may inhibit the release of the cytokine or other chemotactic agent from a cell in the bowel, thus decreasing the number of lymphocytes that are recruited to the bowel. Progesterone and progesterone analogs downregulate the Fc receptors in macrophages. The Fc receptor recognizes antibodies or immune complexes present in an inflammatory process, and such stimulation of the Fc receptor is one of the ways that the macrophage is signaled to release TNF-α and IL-6.

Progesterone analogs with higher "classic progestational activity", as determined by in vitro binding to the uterus or other uterine activity, can provide more effective treatment in the present invention. The presence and extent of classic progesterone activity are determined by the effect of the compound on the uterus. For example, in the rabbit the extent of the effect on the uterine endometrium is determined. Terenius L., Affinities of progestogen and estrogen receptors in rabbit uterus for synthetic progestogens, *Steroids* 23:909–919 (1974); Goth A., Medical Pharmacology, C. V. Mosby Co., St. Louis, p. 429 (1966); Duncan M R, et al., An in vivo study of the action of antiglucocorticoids on thymus weight ratio, antibody titre, and the adrenal pituitary hypothalamus axis, *J. Steroid Biochemistry* 10:245–59 (1979). 17-hydroxyprogesterone and analogs of progesterone that have less progestational classic sex hormone activity may be less effective in the present method. However, derivatives of 17-hydroxyprogesterone that have progestational activity will be effective in the invention.

In one advantageous embodiment, the progesterone or progesterone analog will have low bioavailability, so that much of it will remain in the GI tract, in bowel disorders, or on the skin, for topical psoriasis disorders,;directly treating the diseased tissue. Lower bioavailability may be advantageous because decreased systemic absorption could result in decreased systemic side effects and complications. This could allow patients with chronic conditions to receive treatment for longer periods of time. Although not wishing to be bound by theory, it is believed that the invention may work through a combination of local and systemic effects.

A selective delivery system should provide even more effective treatment. Such a selective delivery system could include an enteric coated tablet or capsule, a low solubility tablet, capsule, suspension, suppository, enema, liquid, foam, cream, gel, ointment, powder, or any of the following forms discussed below. Enteric coatings can be applied to tablets to gain local delivery to various portions of the gastrointestinal tract (for example, upper versus lower). Other coatings can allow for a controlled release of the medication. For example, U.S. Pat. No. 5,458,888, teaches that controlled release dosage forms can be prepared using an external phase of a polyethylene glycol polymer with an average molecular weight of from 3000 to 10000. Additionally, the '888 patent teaches mixing a drug with certain gel forming polymers, allowing for sustained and controlled release in the stomach. The combination of the drug with a non-chemically cross-linked alkyl-substituted cellulose can also provide sustained release in the stomach, according to the method taught in U.S. Pat. No. 5,582,837.

Other techniques allow for delivery of medication to the lower GI tract. Enteric coating materials include cellulose acetate phthalate or a plasticized cellulose acetate phthalate, and are taught in U.S. Pat. No. 5,686,106. Furthermore, pH sensitive capsules can allow for delivery to the more neutral environment of the lower GI tract, as disclosed in U.S. Pat. No. 5,716,648. This can be accomplished by using a coating which is insoluble in gastric juices of a pH below 4, but soluble in intestinal juice exhibiting a pH from 4 to 7. For example, polyvinyl acetate phthalate (PVAP) results in release of active ingredients in the duodenum. Hydroxypropyl methylcellulose phthalate (HPMCP) resists solubility until the environment achieves a pH of at least 5–6. The HPMCP compounds are available in several forms, some providing protection for tablets up to pH 6 and 7, respectively, for release into the colon.

Low solubility formulations can be achieved by mixing the progesterone or progesterone analog with cyclodextrans according to the method presented in U.S. Pat. No. 4,727, 064. These can be used as suspensions, or dried into powders for conversion into tablets, capsules, or other solid dose forms. Certain oils have also been routinely used for suspensions of water insoluble agents to form liquid preparations or gel capsules.

Additionally, the progesterone or progesterone analog can be encapsulated in microspheres by a coating of a cross linked coacervate of gelatin and chondroitin sulfate, allowing for time release of the drug, according to the method taught in U.S. Pat. No. 5,759,582.

Tablets and capsules can be coated with a gum that is broken down by enzymes found in the gut, as disclosed in U.S. Pat. No. 5,656,294. Hydrocolloid gums, obtainable from higher plants, such as guar gum, locust bean gum, gum tragacanth, or karaya gum can be used.

Other strategies for targeted delivery to the colon include those presented in Friend et al, Drug Glycosides: potential prodrugs for colon-specific drug delivery, *J. Med. Chem.* 28:51–57 (1985); Rubenstein, Microbially controlled drug delivery to the colon, *Biopharm & Drug Dispos* 11:465–475 (1990); Salyers et al, Cellular location of enzymes involved in chondroitin sulfate breakdown by Bacteroides thetaiotaomicron, *J. Bacteriol* 143:772–780 (1980). Various strategies for rectal administration of compounds are described in Marshall et al., Putting Rectal 5-Aminosalicylic Acid in its Place: The Role in Distal Ulcerative Colitis, *Am. J. Gastroenterology*, 95:1628–1636 (2000).

Very specific delivery can be achieved by using an enteric feeding tube to deliver the progesterone or progesterone analog composition directly to the inflamed section of the gastrointestinal tract, according to the method presented in U.S. Pat. No. 5,120,306. This technique works especially well for delivery to the proximal small bowel. It could also be applied to the large bowel, either by using an enteric feeding tube or by using similar tubing entering the gastrointestinal tract rectally. For psoriasis, the progesterone or progesterone analog could be topically applied to the lesion, injected into the lesion, or injected into the body near the lesion.

The progesterone or progesterone analogs used in the methods of the present invention may be formulated in a pharmaceutical composition, which may include carriers, thickeners, diluents, buffers, preservatives, surface active agents, tableting agents, liposomes, or lipid formulations, and the like. The pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including on the skin), rectally (by suppository or enema), intranasally, orally, by inhalation, or parenterally, for example by intravenous drip, subcutaneous, intraperitoneal, intramuscular injection, or injection into an area requiring treatment. The activity and metabolism of the composition should be used as a guide when determining the route of administration.

Formulations for topical, rectal, and intranasal administration may include ointments, lotions, creams, gels, drops, enemas, ointments, suppositories, sprays, liquids, and powders. Conventional pharmaceutical carriers, aqueous, powder or oily bases, thickeners, and the like may be necessary or desirable. Compositions for oral administration include powders or granules, suspensions or solutions in water or nonaqueous media, capsules, or tablets. Thickeners, flavorings, diluents, emulsifiers, dispersing aids, tableting agents, or binders may be desirable. Formulations for parenteral administration may include sterile aqueous solutions optionally containing buffers, liposomes, diluents and other suitable additives.

Dosing is dependent on the severity and responsiveness of the condition to be treated, with a course of treatment lasting from several days to several months or until a cure is effected or a diminution of disease state is achieved.

For treatment with an oral composition, in tablet form, for example, dosing is as follows. Optimal dosing schedules and dosing amounts can be calculated based on the severity of the disease and the weight of the patient according to the general guidelines below. Dosages and frequencies would be greater for a patient with a more severe disease state or a higher weight. Depending on the formulation or whether local/targeted delivery is employed, slightly lower doses would be appropriate.

One oral dosing schedule is to treat a patient suffering from inflammatory conditions, including but not limited to, inflammatory bowel disease (ulcerative colitis, Crohn's disease, and proctitis), other noninfectious, inflammatory conditions of the GI tract (microscopic colitis, allergic eosinophilic gastroenteritis, food allergies, pill induced esophagitis, celiac disease, recurrent polyps, and hemorrhoids), and psoriasis, with from about 10 mg to about 5 g, alternatively from about 20 mg to about 4 g, alternatively from about 50 mg to 3 g, alternatively from about 100 mg to 2 g, alternatively from about 500 mg to about 2 g, and alternatively from about 500 mg to about 1 g, total daily dose.

For treatment with a topical composition, applied to the skin as a cream, gel, or lotion, or administered rectally as a cream, foam, enema, or suppository, dosing is as follows. Optimal dosing schedules and dosing amounts can be calculated based on the severity of the disease, the area of skin to be treated (when applied to the skin) or the volume of the rectal administration (when applied rectally). Dosages and frequencies would be greater for a patient with a more severe disease state. Dosages, as percent of active ingredient to vehicle, could be reduced when very large areas of the skin are to be treated, and could be reduced if a larger volume rectal treatment was used (i.e., a larger suppository, for example).

One topical dosing schedule is to treat a patient suffering from inflammatory conditions, including but not limited to, inflammatory bowel disease (ulcerative colitis, Crohn's disease, and proctitis), other noninfectious, inflammatory conditions of the GI tract (microscopic colitis, allergic eosinophilic gastroenteritis, food allergies, recurrent polyps, and hemorrhoids), and psoriasis, with from about 20 mg to about 4 g, alternatively from about 225 mg to about 1.25 g, alternatively from about 550 mg to 750 mg, alternatively about 650 mg, total daily dose.

Both oral and topical dosing can occur once a day, every other day, three times a week, or twice a week. It can also occur in divided doses, twice, three, or four times a day. One acceptable dosing schedule is once a day. Initial treatment can continue for up to 2 weeks for an acute condition, or about 4 weeks to about 16 weeks for a chronic condition, or alternatively about 8 weeks to about 12 weeks for a chronic condition. Longer therapy may also be needed. Patients can be treated for up to six months, or up to one year. Maintenance treatment can last up to or longer than one year.

Patients can be treated on a maintenance basis or on an as needed basis during a problematic episode, depending on the severity of the patient's condition. Patients can also be treated on a rotating treatment basis, where treatment is provided for a period of time and then the patient is given a drug holiday before treatment resumes again. During the drug holiday, patients may receive no treatment, treatment with another mediation or treatment protocol, or treatment with a reduced dosage. Additionally, patients could receive treatment with a higher dose of the composition until a desired reduced disease state is achieved, and then continued on a lower dose of the composition.

Alternatively, the composition could be administered concomitantly with another treatment for the inflammatory conditions. For example, the drug may be administered with aminosalicylic acid (ASA) or another aminosalicylate, including but not limited to, mesalamine. The second drug may be administered in the same composition, or in a different composition. If different compositions are contemplated, the same or different routes of administration could be used depending upon factors including the pharmacokinetics of the compositions, possible interactions, and patient convenience/preference.

EXAMPLES

The following examples are presented for illustrative purposes only and are not intended to limit the scope of the invention in any way.

Example 1

Treatment of Mice With Medroxyprogesterone Acetate

The scid (severe combined immunodeficient) C.B.-17 line of mice provide an effective model of Inflammatory Bowel Disease. The disease state in these mice is triggered by the intraperitoneal injection of CD4+ T cells from a normal BALB/C mouse. The induced disease is characterized by intestinal inflammation in the large intestine, leukocytic infiltrates into the mucosa, submucosa, and mucularis, epithelial cell hyperplasia, loss of mucin-secreting cells, and ulcers with deep fissures, and diarrhea. In the mouse model, CD4+ T cells and macrophages infiltrate the bowel. The scid mouse is recognized by the art as a model for IBD. Powrie et al., Inhibition of Th1 Responses Prevents Inflammatory Bowel Disease in scid Mice Reconstituted with CD45RBhi CD4+ T Cells, *Immunity* 1:553–562 (1994).

500,000 to 1×106 T cells derived from the lymph nodes of normal BALB/C mice were injected intraperitoneally into scid mice 6 weeks prior to sacrifice. 2 days before lymphocyte administration, treatment of the scid mice began with buffer control, medroxyprogesterone acetate, or 17-hydroxyprogesterone. The treatment mice (5 in each group) received 25 mg/kg of drug orally each day until sacrifice. Two BALB/C mice served as an additional negative control for the mouse model, and did not receive the intraperitoneal injections.

After sacrifice, lamina propria (bowel wall) lymphocytes were isolated from each animal. The total number of lymphocytes, number of CD4+ lymphocytes, and the percent of CD4+ lymphocytes was determined. CD4+ lymphocytes were identified by using a first antibody directed to CD4, and a second antibody directed to the first antibody. The second antibody was tagged with fluorescein, which lights up as green in a flow cytometer, identifying which lymphocytes are the CD4+ form. The results are shown in Table 1. Lymphocyte infiltration into the bowel is a predictor of the progress of the disease because lymphocytes are involved in the inflammatory response leading to damage of the bowel wall.

The results show that medroxyprogesterone acetate is effective in decreasing lymphocyte infiltration into the bowel, compared to the buffer control and 17-hydroxyprogesterone. 17-hydroxyprogesterone did not work in treating the mice. This may be due in part to the lesser classic sex organ progestational activity of 17-hydroxyprogesterone, which is believed to be one mode of action of the progesterone analogs in treating IBD. The BALB/C mice show the normal baseline level of lymphocytes in the bowel and the buffer control shows the state of the disease model without any treatment. Table 1 shows the effect of treatment on lymphocytes infiltration in the large bowel lamina propria.

TABLE 1

Effect of treatment on lymphocytes infiltrating the large bowel lamina propria

| Treatment | CD4+ Lymphocytes (1 × 106) | CD4+ as a percent of total Lymphocytes | Total Lymphocytes (1 × 106) |
|---|---|---|---|
| Buffer Control | 19.3 | 89 | 23 |
|  | 22 | 88 | 25 |
|  | 3.2 | 88 | 3.6 |
|  | 22 | 69 | 31.8 |
|  | 32 | 87 | 36.9 |
| Average | 19.7 | 84.2 | 24.1 |
| Medroxyprogesterone Acetate | 1.6 | 81 | 2 |
|  | 4.1 | 87 | 4.8 |
|  | 1.3 | 65 | 2 |
|  | 3.0 | 83 | 3.6 |
|  | 9.2 | 91 | 10.2 |
| Average | 3.8 | 81.4 | 4.5 |
| 17-hydroxyprogesterone | 8.9 | 89 | 10 |
|  | 1.6 | 81 | 2 |
|  | 15 | 93 | 16.5 |
|  | 23 | 91 | 25.2 |
| Average | 16.3 | 88.0 | 18.4 |
| BALB/C mice | 2.2 | 19 | 11.6 |
|  | 0.8 | 18 | 5.4 |
| Average | 1.5 | 18.5 | 8.5 |

Example 2

Effect of Medroxyprogesterone Acetate on Macrophage TNF-α Release

The spleens of six of the mice from Example 1 were removed after the animals were sacrificed. Macrophages were isolated from the spleen of the medroxyprogesterone acetate or buffer control treated mice. TNF-α release from these macrophages was measured by ELISA following stimulation with either (1) rat anti-mouse macrophage Fc receptor antibody 2.4G2 and F(ab')$_2$ IgG goat anti-rat antibody, or (2) phorbol myristate acetate ("PMA"), a phorbol ester. The effect of medroxyprogesterone acetate on TNF-α release is illustrated in Table 2.

TABLE 2

Effect of Medroxyprogesterone Acetate on TNF-α Release

| Mouse | Treatment | Stimulation | TNF-α Measurement (pg/ml) | TNF-α Repeat Measurement (pg/ml) |
|---|---|---|---|---|
| 1 | Buffer | 2.4G2 and F(ab')$_2$ | 2575 | 2053 |
| 2 | | IgG anti-rat | 1873 | 1112 |
| 3 | MPA | | 1843 | 0 |
| 4 | | | 2314 | 1026 |
| 5 | Buffer | 2.4G2 and F(ab')$_2$ | 56220 | 936 |
| 6 | MPA | IgG anti-rat for 1$^{st}$ Measurement and PMA for Repeat Measurement | 27563 | 0 |

Thus, these results suggest that medroxyprogesterone acetate may be inhibiting TNF-α release from macrophages, either by inhibiting its production, release, or down-regulating Fc receptors on the macrophages. Macrophages are involved in inflammatory processes, and infiltrate the bowel wall causing damage in inflammatory bowel diseases.

Example 3

Effect of Medroxyprogesterone Acetate on Macrophage IL-6 Release

The spleens of four of the mice from Example 1 were removed after the animals were sacrificed. Macrophages were isolated from the spleen of the medroxyprogesterone acetate or buffer control treated mice. IL-6 release from these macrophages was measured by ELISA following stimulation with rat anti-mouse macrophage Fc receptor antibody 2.4G2 and F(ab')$_2$ IgG goat anti-rat antibody. The effect of medroxyprogesterone acetate on IL-6 release is illustrated in Table 3.

TABLE 3

Effect of Medroxyprogesterone Acetate on IL-6 Release

| Mouse | Treatment | Stimulation | IL-6 Measurement |
|---|---|---|---|
| 1 | Buffer | 2.4G2 and F(ab')$_2$ IgG anti-rat | 323,406 |
| 2 | | | 310,750 |
| 3 | MPA | | 298,940 |
| 4 | | | 266,557 |

Thus, these results suggest that medroxyprogesterone acetate may be inhibiting IL-6 release from macrophages, either by inhibiting its production, release, or down-regulating Fc receptors on the macrophages. Macrophages are involved in inflammatory processes, and infiltrate the bowel wall causing damage in inflammatory bowel diseases.

Example 4

Treatment of Patients With Ulcerative Colitis

Patients with mild to moderate ulcerative colitis were evaluated for their response to treatment with medroxyprogesterone acetate. Patients in the treatment group (8 patients) received a loading dose of 1 gram of medroxyprogesterone acetate every 6 hours for 8 doses. These patients were then given 500 mg of medroxyprogesterone every 12 hours for 8 weeks.

Disease improvement was measured using the Disease Activity Index (DAI). The DAI is a total score for stool frequency, blood in the stool, the investigator's global assessment (IGA), and the physician's evaluation of the appearance of mucosa during flexible sigmoidoscopy of the colon. Patients showed improvement if they had a reduction of one or more units in the DAI score at the end of the study, when compared to baseline. Table 4 shows patient improvement with treatment.

TABLE 4

Patient Improvement with Treatment for Ulcerative Colitis

| Patient Number | Improvement |
|---|---|
| 1 | Yes |
| 2 | No |
| 3 | Yes |
| 4 | No |
| 5 | Yes |
| 6 | Yes |
| 7 | Yes |
| 8 | No |

Thus, medroxygesterone acetate represents a good treatment for ulcerative collitis. Five out of eight patients showed improvement with treatment (8 weeks). Of the 3 patients who did not respond at the end of the 8 week study, 2 patients demonstrated a reduction in symptoms and complaints during initial treatment.

Example 5

Treatment of Patients With Crohn's Disease

Patients with mild to moderate Crohn's disease were evaluated for their response to treatment with progesterone acetate. Patients in the treatment group (12 patients) recieved a loading dose of 1 gram of medroxyprogesterone acetate every 6 hours for 8 doses. These patients were then given 500 mg of medroxyprogesterone every 12 hours for 8 weeks.

Disease improvement was measured using the Crohn's Disease Activity Index (CDAI). The CDAI score for a patient was calculated by multiplying the numerical value for each variable by multiplication factor indicated for that variable, and totaling all of the resultant values, as shown in Table 5. A score below 150 indicated remission and a score above 450 indicated severe disease. In order to enter the study, patients were required to have a total CDAI score of 200 to 400 at baseline.

TABLE 5

Determination of CDAI Score

| Variable | Multiplication Factor |
|---|---|
| Number of liquid or soft stools (over 7 days) | 2 |
| Abdominal pain (sum of scores over 7 days) 0 = none, 1 or 2 = intermediate, 3 = severe | 5 |
| General well-being (sum of scores over 7 days) 0 = good to 4 = terrible | 7 |
| Number of complications (on day of assessment except for fever) arthalgias or arthritis iritis or uveitis erythema nodosum, pyoderma gangrenosum, or aphthous stomatits anal fissure, fistula, or abscess other fistula fever (>37.8° C., over 7 days) | 20 |

TABLE 5-continued

Determination of CDAI Score

| Variable | Multiplication Factor |
|---|---|
| Use of opiates for diarrhea<br>0 = no, 1 = yes | 30 |
| Abdominal Mass (on day of assessment)<br>0 = none, 2 = questionable, 5 = definite | 10 |
| 47 minus hematocrit (men), 42 minus<br>hematocrit (women) (day of assessment) | 6 |
| Percentage deviation above or below standard<br>weight (on day of assessment) according to the<br>Metropolitan Life Insurance Height and Weight<br>Tables for Men and for Women | 1 |

Disease remission was defined as a CDAI score of 150 or below. Disease response was defined as either a decrease of 70 or greater in the CDAI or disease remission. Table 6 shows patient response to treatment.

TABLE 6

Patient Response to Treatment for Crohn's Disease

| Patient Type | Number of Patients | Remissions | Responders |
|---|---|---|---|
| Completers | 10 | 7 | 8 |
| Ongoing | 1 | — | — |
| Drop out | 1 | — | — |

Of the patients treated, eight out of ten responded to therapy (8 weeks). One patient dropped out for a minor adverse event (fatigue) and had no efficacy data. The remaining patient is still continuing on the study. Thus, medroxyprogesterone acetate represents a good treatment for Crohn's disease.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. All of the documents cited within this application are hereby incorporated by reference.

I claim:

1. A method of treating a patient suffering from at least one of the following inflammatory conditions: ulcerative colitis, Crohn's disease, proctitis, microscopic colitis, allergic eosinophilic gastroenteritis, food allergies, pill induced esophagitis, celiac disease, recurrent polyps, and hemorrhoids, wherein a progesterone analog is selected from medroxyprogesterone acetate and said progesterone analog is administered to the patient.

2. The method of claim 1, wherein the patient is treated with medroxyprogesterone acetate once a day.

3. The method of claim 1, wherein the patient is treated with from about 500 mg to about 2 grams of medroxyprogesterone acetate daily.

4. The method of claim 1, wherein the medroxyprogesterone acetate is administered orally.

5. The method of claim 1, wherein the patient is suffering from at least one of the following inflammatory conditions of the patient's gastrointestinal tract: ulcerative colitis, Crohn's disease, proctitis, microscopic colitis, allergic eosinophilic gastroenteritis, food allergies, recurrent polyps, and hemorrhoids.

6. The method of claim 5, wherein the medroxyprogesterone acetate is formulated in an entedc coated tablet to allow for targeted delivery to an affected portion of the gastrointestinal tract.

7. The method of claim 5, wherein the medroxyprogesterone acetate is administered rectally using a composition chosen from an enema, a suppository, a foam, a cream, a gel, an ointment, and a suspension.

* * * * *

UNITED STATES PATENT AND TRADEMARK OFFICE
CERTIFICATE OF CORRECTION

PATENT NO. : 6,610,674 B1  Page 1 of 1
DATED : August 26, 2003
INVENTOR(S) : Alan Schreiber It is certified that error appears in the above-identified patent and that said Letters Patent is hereby corrected as shown below:

Column 14,
Line 31, "entedc" should read -- enteric --

Signed and Sealed this

Second Day of December, 2003

JAMES E. ROGAN
*Director of the United States Patent and Trademark Office*